US009834765B2

(12) United States Patent
Bergmann et al.

(10) Patent No.: US 9,834,765 B2
(45) Date of Patent: Dec. 5, 2017

(54) SEQUENCE TAGS

(71) Applicant: Roche Diagnostics Operations, Inc., Indianapolis, IN (US)

(72) Inventors: Frank Bergmann, Iffeldorf (DE); Bruno Frey, Penzberg (DE); Dieter Heindl, Paehl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 771 days.

(21) Appl. No.: 14/200,325

(22) Filed: Mar. 7, 2014

(65) Prior Publication Data

US 2014/0256566 A1 Sep. 11, 2014

(30) Foreign Application Priority Data

Mar. 8, 2013 (EP) ..................... 13158348

(51) Int. Cl.
*C12Q 1/68* (2006.01)
*C12N 15/10* (2006.01)
*C07H 21/04* (2006.01)

(52) U.S. Cl.
CPC ....... *C12N 15/1065* (2013.01); *C12Q 1/6806* (2013.01); *C12Q 1/6848* (2013.01); *C12Q 1/6853* (2013.01); *C12Q 1/6855* (2013.01); *C12Q 1/6869* (2013.01); *C12Q 1/6874* (2013.01)

(58) Field of Classification Search
None
See application file for complete search history.

(56) References Cited

U.S. PATENT DOCUMENTS

2012/0220494 A1\* 8/2012 Samuels ............ C12N 15/1075
506/16

FOREIGN PATENT DOCUMENTS

WO 2008/061193 A3 5/2008

OTHER PUBLICATIONS

Extended European Search Report dated Jul. 24, 2013, in Application No. EP13158348.6, 6 pages.
Hysom, David A. et al., "Skip the Alignment: Degenerate, Multiplex Primer and Probe Design Using K-mer Matching Instead of Alignments," PLoS One, Apr. 2012, e34560, 12 pages, vol. 7, Issue 4.
Jayaprakash, Anitha D. et al., "Identification and remediation of biases in the activity of RNA ligases in small-RNA deep sequencing," Nucleic Acids Research, Nov. 2011, pp. 1-12, vol. 39, No. 21.
Liang, Richard A. et al., "Impact of experimental conditions on the utility of 'primer ID' tagging for next-generation HIV sequencing," Conference on Retroviruses and Opportunistic Infections Poster 0-128, Mar. 6, 2013, Atlanta, Georgia.

\* cited by examiner

*Primary Examiner* — Nancy J Leith
(74) *Attorney, Agent, or Firm* — Roche Sequencing Solutions, Inc.

(57) ABSTRACT

Provided herein is a new class of nucleic acid tagging molecules which are essentially free of homopolymer stretches. The tagging molecules can tag a plurality of individual target molecules for detection with a high degree of accuracy. The tagging molecules can be used to tag at least 105 or 106 individual target molecules. The tagged individual target molecules can be subjected to high throughput sequence analysis.

8 Claims, 5 Drawing Sheets

SEQUENCE TAGS

FIELD OF INVENTION

The invention relates to the field of tagging individual nucleic acid molecules. More precisely the invention relates to the field of tagging individual nucleic acids that are subsequently subjected to high throughput sequence analysis.

BACKGROUND OF THE INVENTION

Due to the recent availability of next generation sequencing systems, amplicon sequencing and ultra deep sequencing have become a powerful analytic tool for mutational analysis. Ultra deep sequencing requires sequencing of many individual molecules derived from and representing a polymorphic target sequence. In particular, ultra deep sequencing allows for detection and quantification of minority species sequences of a certain target nucleic acid within a background of wildtype sequences. For example, such detection and quantification is particularly useful for detection of residual tumor cells in the field of oncology, or for the detection of drug resistancies in the field of virology.

However, ultra deep sequencing always requires a step of amplification of the target nucleic acid sample to become analyzed. During this amplification, errors are introduced with a certain degree of frequency during the polymerase catalyzed PCR process. As a consequence, such artificially introduced sequence changes usually can not be discriminated from minority species sequences such as real mutations or sequence alterations that only exist within the sample to become analyzed with low abundancy (Vandenbroucke et al., Biotechniques 2011, 51 (3), 167-177).

One possibility to overcome this issue is the tagging of each individual target nucleic acid molecule derived from the sample prior to amplification with a unique nucleic acid sequence. In the art, such a tag is termed UID sequence (Unique sequence Identifier).

For example, Jabara et al. (PNAS 2011, 108 (50), 20166-20171) disclose the introduction of a random sequence tag in the initial amplification primer. As a consequence, subsequent sequencing allows to identify all sequence reads which are derived from the same individual target molecule originally contained within the sample. Jabara et al. used an 8mer wobble tag consisting of all 4 nucleotides resulting 65536 unique different sequence tag sequences. This approach, however, has the disadvantage that due to too low number of different tag sequences identical tag sequences will be tagged to different target sequences making the UID approach in such cases redundant (Sheward et al., PNAS 2012, 109 (21), E1330).

Similarly, WO 2012/0388239 and its equivalent US2012/0071331 disclose a method of estimating the number of starting polynucleotide molecules sequenced using degenerate UID sequences (in the applications termed "DBR"). The claimed method always comprises the steps of a) tagging, b) pooling c) amplification and d) sequencing. The references also disclose application of such a method of attaching individual UID tags to individual sequences from a polymorphic region, deep sequencing and subsequent allele calling.

Identification and quantification of rare sequence variants within a high wildtype background requires a high degree of accuracy in particular when such an analysis is performed within a diagnostic setting. However, the use of completely randomized individual sequence tags comprises certain disadvantages with a negative impact on the accuracy of tag identification.

First of all, tags comprising homopolymer stretches within a UID sequence cannot be read with high accuracy using commercially available sequencing by synthesis platforms such as the 454 Genome Sequencer system or the Ion Torrent Proton system. Secondly, particular stretches such as G tetrads strongly interfere with PCR amplification. Thirdly, complementary homopolymer stretches result in partially self complementary sequence tags, leading to undesired side reactions during an amplification or a subsequent sequencing reaction.

A further disadvantage of the state of the art is that tagging of each individual target sequence with a unique sequence tag is not accomplished and known as "birthday problem" (Sheward et al., PNAS 2012, 109 (21), E1330).

Thus it is an object of the present invention to provide a solution for ultra deep sequencing applications with improved sequence tags.

SUMMARY OF THE INVENTION

The present invention provides a plurality of oligonucleotides comprising a degenerated sequence segment, said plurality being characterized in that it does not comprise a homopolymer stretch longer than 3 nucleotide residues in the degenerated sequence segment. Such a plurality of oligonucleotides may comprise at least $10^5$ and preferably at least $10^6$ individual molecules.

Said segment may comprise one subsegment or more than one identical subsegments, said subsegments having the sequence X1-X2-X3-X4, characterized in that X1 is a degenerated base comprising a first set of three different bases or base analogs, X2 is a degenerated base comprising a second set of three different bases or base analogs, X3 is a degenerated base comprising a third set of three different bases or base analogs, and X4 is a degenerated base comprising a fourth set of three different bases or base analogs, wherein said first, second, third and fourth set are different from each other.

Said plurality of oligonucleotides may comprise also a plurality of 2 or more subsegments. Such a plurality of subsegments may comprise at least 2 identical subsegments.

The present invention is also directed to the use of a plurality of oligonucleotides as described above for tagging individual molecules. Said individual molecules may be nucleic acid molecules.

Thus, the present invention also provides a method for tagging individual nucleic acid molecules, comprising the steps of (i) providing a plurality of individual molecules, (ii) adding a plurality of oligonucleotides as disclosed above, and (iii) attaching one representative of said plurality of oligonucleotides to one representative each of said plurality of individual molecules, which may be nucleic acid molecules.

The attachment may, for example, be achieved by means of ligating said plurality of oligonucleotides to said plurality of individual molecules. The attachment may also be achieved by means of hybridizing a target binding site located downstream of said degenerated sequence segment to the plurality of individual molecules. If the latter is the case, then said plurality of individual oligonucleotides may be elongated by means of performing a target dependent DNA polymerase catalyzed primer extension reaction.

The present invention also provides a method for determining the sequence of a plurality of individual nucleic acid molecules comprising the steps of (i) tagging said plurality of individual nucleic acid molecules each with an individual representative as disclosed above, (ii) amplifying said tagged plurality of individual molecules, and (iii) sequencing said amplified individual molecules.

A preferred embodiment of such a method involves the use of said plurality of individual nucleic acid molecules represents one or more identical nucleic acid analyte regions. Then the new method may further comprise the step of generating a consensus sequence from the sequences determined from the different sequence reads for each nucleic acid analyte region. Also, the method is applicable for a method of allele calling, comprising the steps of (i) performing the inventive method on a plurality of individual nucleic acid molecules representing one or more identical nucleic acid analyte regions, (ii) comparing said sequence reads derived from each tagged individual nucleic acid molecule with the wildtype sequence of said nucleic acid analyte region, and (iii) determining a mutation if all sequence reads derived from each tagged individual nucleic acid molecule each comprising different tag sequences are identical to each other, but different to the wildtype sequence.

DETAILED DESCRIPTION OF THE INVENTION

Definitions

Figure 1:
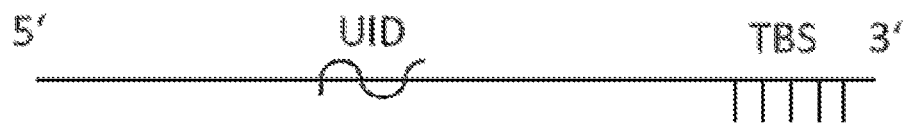
FIG. 1. Schematic drawing of a plurality of oligonucleotides according to the present invention comprising a degenerate sequence element (UID) and a target binding site (TBS).

The term "amplicon" generally refers to selected amplification products which are amplified by a specific set of forward and reverse primers such as those produced from amplification techniques known in the art.

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification.

The term "complementary" generally refers to the ability to form favorable thermodynamic stability and specific pairing between the bases of two nucleotides at an appropriate temperature and ionic buffer conditions. This pairing is dependent on the hydrogen bonding properties of each nucleotide. The most fundamental examples of this are the hydrogen bond pairs between thymine/adenine and cytosine/guanine bases. In the present invention, primers for amplification of target nucleic acids can be both fully complementary over their entire length with a target nucleic acid molecule or "semi-complementary" wherein the primer contains an additional, non-complementary sequence minimally capable or incapable of hybridization to the target nucleic acid.

The term "hybridize" generally refers to the base-pairing between different nucleic acid molecules consistent with their nucleotide sequences. The terms "hybridize" and "anneal" can be used interchangeably.

The term "nucleic acid" generally refers to both DNA or RNA, whether it may be a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3' or 5' overhangs and as such are not required or assumed to be completely double-stranded over their entire length. Furthermore, the term nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; phosphorothioate, methylphosphonates, phosphoroamidates and phosphorotriester linkages between nucleotides to prevent degradation; methylation; and modified bases such as deoxyinosine, 5-bromo dU, deoxyuridine, 2-aminopurine, dideoxycytidine, 5-methyl dC, locked nucleic acids (LNA's), iso-dC and -dG bases, 2'-O-methyl RNA bases and fluorine modified bases.

The term "oligonucleotide" generally refers to a nucleic acid sequence typically designed to be single-stranded DNA and less than 100 nucleotides in length.

The term "primer" generally refers to an oligonucleotide that is able to anneal, or hybridize, to a nucleic acid sequence and allow for extension under sufficient conditions (buffer, dNTP's, polymerase, mono- and divalent salts, temperature, etc.) of the nucleic acid to which the primer is complementary.

The term "tag sequence" generally refers to the sequence of the forward and reverse primers of the first primer set at their 5' ends and the sequence of the forward and reverse primers of the second primer set at the 3' ends.

The terms "template nucleic acid", "template molecule", "target nucleic acid", and "target molecule" can be used interchangeably and refer to a nucleic acid molecule that is the subject of an amplification reaction that may optionally be interrogated by a sequencing reaction in order to derive its sequence information.

The terms "template specific region", "target specific region" or "region of interest" can be used interchangeably and refer to the region of a particular nucleic acid molecule that is of scientific interest. These regions typically have at least partially known sequences in order to design primers which flank the region or regions of interest for use in amplification reactions and thereby recover target nucleic acid amplicons containing these regions of interest.

Details of the Invention

The present invention provides oligonucleotides comprising improved UID sequences for tagging individual target molecules. Generally speaking, the oligonucleotides represent a pool of individual oligonucleotide molecules, which is generated by means of a conventional chemical oligonucleotide synthesis method as it is well known in the art. Typically, for obtaining an oligonucleotide population with a defined sequence, one particular building block only, representing a certain base selected from A, G, C and T is added per synthesis cycle.

The sequence diversity of the individual molecules within an oligonucleotide population is achieved by means of applying the "wobbling concept". For this concept, during at least one synthesis cycle, the synthesis reaction is executed by adding more than one type of nucleoside building block, e.g. nucleoside phosphoramidite in parallel. Thus, pluralities of oligonucleotides with degenerated sequences can be synthesized within one typical oligonucleotide synthesis set up. A preferred oligonucleotide synthesis method is based on conventional phosphoramidite chemistry and well known in the art. Respective synthesizer instruments and reagents are commercially available.

The plurality of oligonucleotides according to the present invention thus comprises a degenerated sequence segment. However, in contrast to what is disclosed in the art, said segment is not a fully degenerated sequence. It is further characterized in that it does not comprise a homopolymer stretch longer than 3 nucleotide residues in the degenerated sequence segment.

If according to what is disclosed in the art, 4 different building blocks are used, then homopolymer stretches of identical nucleotide residues cannot be excluded. In contrast, for example, the use of 4 different wobbles consisting of only 3 nucleotides at certain positions X1 (A/G/C), X2 (A/G/T), X3 (A/C/T), X4 (G/C/T) leads to oligonucleotides which do not contain more than 3 consecutive bases.

This feature is achieved by an appropriate programming of the oligonucleotide synthesizer instrument or by using pre-mixed mixtures of more than 1 but less than 4 different nucleoside building blocks as individual monomeric building block. At certain positions of the nascent oligonucleotide addition of more than 1 but less than 4 different building blocks is arranged resulting in a certain degree of limited wobbling. Several alternatives are possible and will be disclosed below.

For ultra deep sequencing applications, it is advantageous, if the plurality of oligonucleotides comprises at least $10^5$ and preferably at least $10^6$ individual molecules. This, of course requires a certain minimal length of the degenerated sequence segment.

The degenerated sequence segment may comprise one or more identical subsegments. The subsequents have the sequence
X1-X2-X3-X4,
characterized in that X1 is a degenerated base comprising a first set of three different bases or base analogs, X2 is a degenerated base comprising a second set of three different bases or base analogs, X3 is a degenerated base comprising a third set of three different bases or base analogs, and X4 is a degenerated base comprising a fourth set of three different bases or base analogs, wherein said first, second, third and fourth set are different from each other.

Alternatively, said subsegments may have the sequence selected from a group consisting of
X-N1-X-N2-X-N3-X-N4-,
X-N1-X-N2-X-N3- and
X-N1-X-N2-,
characterized in that X is a fully degenerated base comprising a set of four different bases or base analogs, and N1, N2, N3, and N4 are different bases each.

Also alternatively, the subsegments may have the sequence
X-Y1-X-Y2-X-Y1-X-Y2-,
characterized in that X is a fully degenerated base comprising a set of four different bases or base analogs, and Y1 is a degenerated base comprising a first set of two different bases or base analogs and Y2 is a degenerated base comprising a second set of two different bases or base analogs not occurring in Y1.

Also alternatively, the subsegments have a sequence selected from a group consisting of
X1-X2,
X1-X2-X3,
X1-X2-X3-X4,
X1-X2-X3-X4-X5 and
X1-X2-X3-X4-X5-X6,
characterized in that X1 to X6 are degenerated bases comprising a first set of two different bases or base analogs, X2 is a degenerated base comprising a second set of two different bases or base analogs, X3 is a degenerated base comprising a third set of two different bases or base analogs, X4 is a degenerated base comprising a fourth set of two different bases or base analogs, X5 is a degenerated base comprising a fifth set of two different bases or base analogs and X6 is a degenerated base comprising a sixth set of two different bases or base analogs, wherein said first, second, third, fourth, fifth and sixth set are different from each other.

In order to increase the number of different tags obtainable, it is favourable to use a rather long degenerated sequence segment. Such a segment within a plurality of oligonucleotides may comprise at least 2 subsegments which may be different or identical. All subsegments may be located in repetitive form one after another preferably without any intermediate nucleotide residue. In one embodiment the at least 2 subsegments are identical and located in repetitive form one after another without any intermediate nucleotide residue.

The number of subsegments may be adjusted to the tagging application, for which said plurality of oligonucleotides shall be used. Typically, said plurality of oligonucleotides comprises between 3 and 8 subsegments. In one particular embodiment, it comprises 5 subsegments.

The number of nucleotide residues within said degenerate base sequence segment may also vary and become adjusted to the specific type of application envisaged. Typically, said degenerate base sequence segment comprises 12-40 nucleotide residues. Preferably, said segment comprises 16-32 and most preferably between 20-24 nucleotides.

In addition to the degenerate base sequence segment, the plurality of oligonucleotides may comprise one or more additional sequence elements with other functionalities.

In one embodiment, such an element is a primer binding site which is complementary to a site within a target nucleic acid that subsequently shall be amplified using said plurality of oligonucleotides as a primer. If the amplicon shall contain a respective individual sequence tag, then the primer binding site which is complementary to the target needs to be located 3' downstream of the degenerate base sequence element. Thus, the present invention also provides a plurality of oligonucleotides as disclosed above, wherein said segment is located 5' upstream of target binding site. A schematic drawing is shown in FIG. 1. "UID" represents the degenerate sequence segment. "TBS" represents the target binding site.

Figure 2:
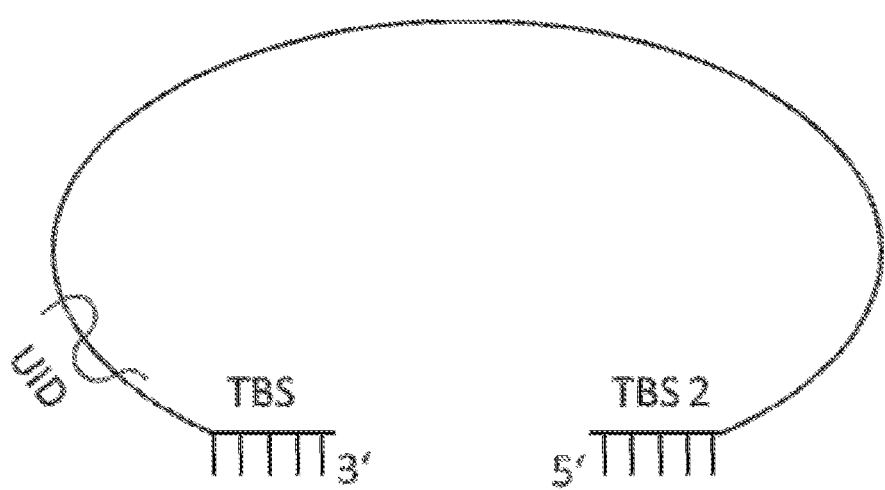
FIG. 2. Schematic drawing of a plurality of oligonucleotides according to the present invention which are MIP probes. "UID" represents the degenerate sequence segment. "TBS" represents the 3' proximal target binding site. "TBS2" represents the 5' proximal target binding site.

In a particular embodiment, said plurality of oligonucleotides are so called MIP probes. MIP probes are hybridization probes with a 3' terminal site which hybridizes to a target nucleic acid and an additional 5' terminal target binding site which hybridizes in close vicinity 3' downstream of the target sequence of the first binding site. MIP probes are disclosed in detail in Roak et al., Science 2012, Vol. 388, p. 1619-1622. A schematic drawing is shown in FIG. 2. "UID" represents the degenerate sequence segment. "TBS" represents the 3' proximal target binding site. "TBS2" represents the 5' proximal target binding site.

Optionally said 5' terminal target binding site is phosphorylated at the 5' terminus. This enables for elongating the MIP probe by means of a primer extension reaction using the target nucleic acid as a template and subsequent circularization of the MIP probe by means of ligation. The segment representing the newly synthesized complement of the target nucleic acid can then be amplified by means of an inverse PCR and subjected to further analysis.

Figure 3:
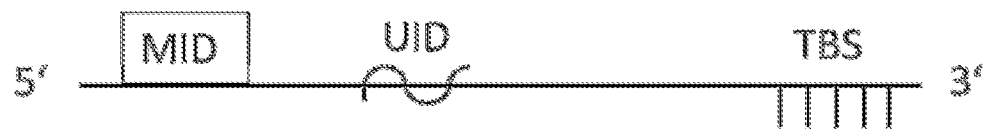
FIG. 3. Schematic drawing of two embodiments of a plurality of oligonucleotides according to the present invention comprising a sample specific MID sequence. "UID" represents the degenerate sequence segment. "MID" represents the sample specific sequence segment. "TBS" represents a target binding site.

Another additional sequence element which a plurality of oligonucleotides according to the present invention may comprise a so-called MID segment. Such MID segment is a sample specific sequence element. Thus, the present invention also provides a set of pluralities of oligonucleotides with a degenerate sequence segment, characterized in that each member of that said set comprises a unique sequence element, i.e. the MID segment. When used for analytical approaches, each different member of said set is brought into contact with a different sample. Subsequently the samples may become pooled and identification of the MID sequence tag allows to determine the origin of the respectively tagged analyte. Typically, said MID segment needs to be located 5' upstream of the degenerate sequence segment. A schematic drawing is shown in FIG. 3. "UID" represents the degenerate sequence segment. "MID" represents the sample specific sequence segment. "TBS" represents the 3' proximal target binding site. Each member of said set of plurality of oligonucleotides may require a separate oligonucleotide synthesis reaction.

Figure 4:
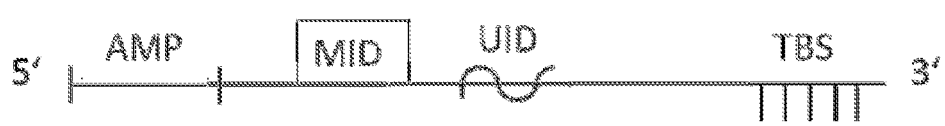
FIG. 4. Schematic drawing of different embodiments of a plurality of oligonucleotides according to the present invention. "UID" represents the degenerate sequence segment. "MID" represents the sample specific sequence segment. "SEQ" indicates a sequencing primer site and "AMP" represents an amplification primer site.
Figure 4:
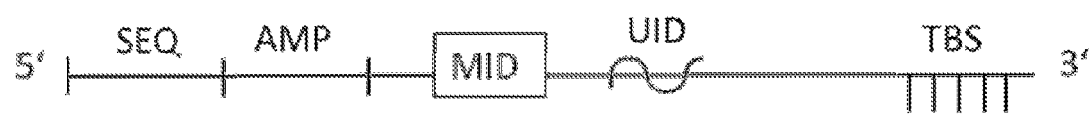
Figure 4:
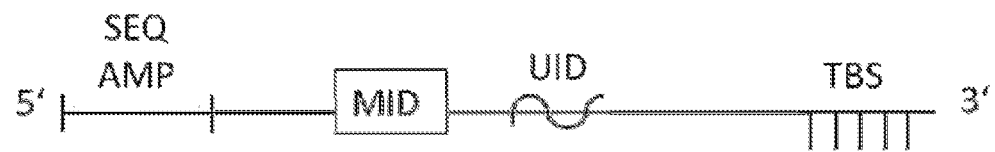

A further additional sequence element which a plurality of oligonucleotides according to the present invention may comprise is a site representing a primer sequence. The primer sequence, for example, may be a primer that can be used for a subsequent PCR amplification reaction. The primer sequence may also represent a primer that can be used for a subsequent sequencing reaction. The primer site may also represent a primer that can be used for both, amplification and sequencing. Also, the additional sequence element may comprise two separate primers, one being able to act as a sequencing primer and the other being able to act as an amplification primer. In this case, the sequence element representing a sequencing primer is typically located 3' downstream of the element representing an amplification primer. Thus, the present invention also provides a plurality of oligonucleotides as disclosed above, wherein said degenerate sequence segment is located 3' downstream of a sequencing primer element, or 3' downstream of an amplification primer element. These different embodiments are schematically shown in FIG. 4. "UID" represents the degenerate sequence segment. "MID" represents the sample specific sequence segment. "SEQ" indicates a sequencing primer site and "AMP" represents an amplification primer site.

Figure 5:
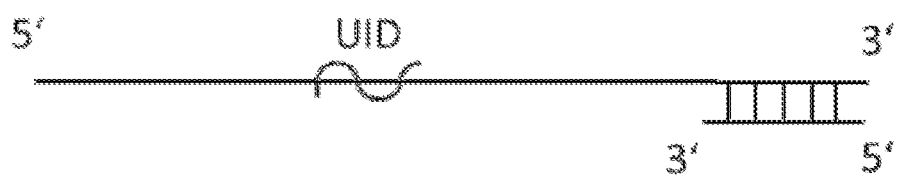
FIG. 5. Schematic drawing of a plurality of oligonucleotides according to the present invention which comprises a double stranded 3' terminus for ligation to the pool of target nucleic acids.

In a particular embodiment, the plurality of oligonucleotides according to the present invention comprises a common additional segment located at the 3' terminus, to which a complementary oligonucleotide is hybridized. Such a partially double stranded pool of oligonucleotides may become attached with high efficiency to a pool of double stranded DNA fragments that shall become tagged (FIG. 5).

Depending on their specific actual design, the inventive plurality of oligonucleotides may be used for a variety of different purposes. In general, said plurality of oligonucleotides is used to tag individual molecules that are present in a sample. Typically, the sample is a biological sample derived from any possible source. Depending on the use of an appropriate attachment method, the inventive plurality of oligonucleotides may be used to label any type of biological molecules.

Predominantly, the inventive plurality of oligonucleotides will be used for tagging nucleic acids molecules. Typically said nucleic acid molecules are selected from a group consisting of double stranded DNA, single stranded DNA, single stranded RNA, double stranded RNA and double stranded RNA/DNA hybrids.

For sequencing applications, it may be advantageous to tag single stranded DNA molecules. Also for sequencing applications, an individual tagging is extremely advantageous if an individual representative of the same polymorphic target region shall be analyzed. Typically, such representatives typically have at least 90% and preferably 98% sequence identity. In some cases, said representatives may only differ from each other with respect to one or more single nucleotide polymorphisms (SNPs).

The present invention not only provides a plurality of oligonucleotides according to the present invention comprising a degenerated sequence segment which does not comprise a homopolymer stretch longer than 3 nucleotide residues in the degenerated sequence segment, but also a variety of appropriate methods for using them in order to tag individual molecules.

Thus in one aspect, the present invention provides a method for tagging individual nucleic acid molecules, comprising the steps of
  providing a plurality of individual molecules,
  adding any plurality of oligonucleotides as disclosed above
  attaching one representative of said plurality of oligonucleotides to one representative each of said plurality of individual molecules.

Preferably, said molecules are nucleic acid molecules. Said molecules are selected from a group consisting of double stranded DNA, single stranded DNA, single stranded RNA, double stranded RNA and double stranded RNA/DNA hybrids.

In one embodiment, said step of attaching is achieved by means of ligating said plurality of oligonucleotides to said plurality of individual molecules. In a particular embodiment, when the plurality of oligonucleotides according to the present invention comprises a common additional segment located at the 3' terminus, to which a complementary oligonucleotide is hybridized, such a partially double stranded pool of oligonucleotides may become ligated with high efficiency to a pool of double stranded DNA fragments that shall become tagged. Most ligases known in the art can be used for the ligation reaction. Alternatively, when the plurality of oligonucleotides does not comprise any double stranded segment, then a specific ligase which ligates single stranded DNA substrates such as T4 ligase can be used.

Alternatively, attachment of the plurality of oligonucleotides according to the invention is achieved by means of hybridizing a target binding site located 3' downstream of said degenerated sequence segment to the plurality of individual nucleic acid molecules.

In addition the inventive method may further comprise a step of elongating said plurality of individual oligonucleotides by means of performing a target dependent DNA polymerase catalyzed primer extension reaction. In a particular embodiment, said plurality of oligonucleotides are so called MIP probes having a 3' terminal site which hybridizes to a target nucleic acid and an additional 5' terminal target binding site which hybridizes in close vicinity 3' downstream of the target sequence of the first binding site (FIG. 2). The 5' terminal target binding site needs to be phosphorylated at the 5' terminus. In this case, after subsequent DNA polymerase catalyzed primer extension reaction, the 5' end of an individual oligonucleotide is ligated to the 3' end of the product generated by said primer extension reaction. The segment representing the newly synthesized complement of the target nucleic acid can then be amplified by means of an inverse PCR and subjected to further analysis.

Tagging of individual molecules prior to amplification is extremely important in the context of sequencing analyses, because for different sequence reads it can become determined whether they are derived from the same or different original individual target molecule. In particular, this is of interest when a sequence analysis of individual molecules all derived from the same polymorphic region of a particular gene is performed.

Thus, the present invention also provides a method for determining the sequence of a plurality of individual nucleic acid molecules comprising the steps of
    tagging said plurality of individual nucleic acid molecules each with an individual representative according to any of the methods disclosed above
    amplifying said tagged plurality of individual molecules, and
    sequencing said amplified individual molecules.

The method according to the present invention advantageously includes the sequence determination of each individual sequence tag. The sequence determination may be done by any methodology known in the art wherein the sequence of individual molecules that have been clonally amplified can be determined. For example sequence determination can be done using the commercially available Hiseq and MySeq instruments (Illumina), the Ion Torrent PGM or Ion Torrent Proton systems (Life Technologies) or the GS FLX and GSJunior systems (454 Life Sciences).

In particular, the present invention also provides a method for determining the sequence of a plurality of individual nucleic acid molecules, said molecules being characterized in that said individual molecules are derived from and represent the same polymorphic target region. Typically, such individual molecules have at least 90% and preferably 98% sequence identity. In some cases, said representatives may only differ from each other with respect to one or more single nucleotide polymorphisms (SNPs).

Such a method is understood in the art as ultra deep sequencing. Ultra deep sequencing requires sequencing of many individual molecules derived from and representing a polymorphic target sequence, thereby enabling the detection and quantification of minority species sequences of a certain target nucleic acid within a background of wildtype sequences. For ultra deep sequencing, sequence reads derived from the multiple amplified copies of a single species of nucleic acid molecule are generated and analyzed.

In order to discriminate sequence changes artificially introduced during the amplification step from real sequence alterations of real minority species, the sequence information derived from the sequence tags are analyzed.

In one embodiment, the method for determining the sequence of a plurality of individual nucleic acid molecules using a plurality of sequence tags according to the present invention further comprises the step of counting the number of differently tagged sequence reads. As a consequence, the number of different target sequences present in the original sample can be estimated. If the different target sequences are derived from the same polymorphic region, the number of isoforms from the same polymorphic region as present in the original sample can be determined.

The inventive method for sequence determination not only allows for the analysis of one particular nucleic acid analyte region, representing a polymorphic target sequence. It is also possible to tag different nucleic acid analyte regions in parallel. Thus, typically, said plurality of individual nucleic acid molecules represents not more than one identical nucleic acid analyte region. However, it is also within the scope of the invention, if said plurality of individual nucleic acid molecules represents more than one identical nucleic acid analyte region.

In a second embodiment which may or may not be combined with the previous embodiment, the method for determining the sequence of a plurality of individual nucleic acid molecules using a plurality of sequence tags according to the present invention further comprises the step of counting the number of sequence reads obtained for each tag. This information is important because it indicates how many times a particular individual sequence that was present in the original sample has been sequenced.

The method according to the second embodiment may further comprise the step of generating a consensus sequence from the sequences determined from the different sequence reads for each nucleic acid analyte region. Building of the consensus sequence is possible according to standard algorithms well known in the art.

The method according to the second embodiment may also be used for a method of allele calling. In this case, the method further comprises the steps of
    comparing said sequence reads derived from each tagged individual nucleic acid molecule with the wildtype sequence of said nucleic acid analyte region, and
    determining a mutation if all sequence reads derived from each tagged individual nucleic acid molecule each comprising different tag sequences are identical to each other, but different to the wild type sequence.

For example, an allele call, i.e. the existence of a defined nucleotide or a defined nucleotide sequence at a given position may be identified as follows:
a) Generate multiple sequence reads from individual nucleic acid molecules all comprising the same sequence tag
b) Set a cut off value for identification of a true allele regarding the percentage of reads which identify a particular allele (in instances where high accuracy is required, the cut off level may be 100%)
c) Determine the presence or absence for said allele in all sequence reads comprising the same tag
d) Determine whether the percentage of reads exceeds the pre-set cut off value.

Finally, the present invention is also directed to a method of synthesizing the plurality of oligonucleotides disclosed above. In a particular embodiment, the quality of the plurality of oligonucleotides may become further improved by means of depleting a particular sequence. Such a depletion is achieved by means of hybridizing said plurality of oligonucleotides with a pool of nucleic acids with sequences that are complementary to those sequences which are undesired. Subsequently, the hybridization complexes are separated from the plurality of oligonucleotides and said plurality of oligonucleotides is then ready for use.

Preferably, said pool of nucleic acids with sequences that are complementary to those sequences which are undesired is immobilized on a solid support, such as a chromatographic column. The plurality of oligonucleotides according to the present invention may then be loaded onto the column, hybridization may occur and the plurality of desired oligonucleotides, which does not hybridize to the immobilized nucleic acids may simply become diluted.

The following examples 1 and 2 are provided to aid the understanding of the present invention, the true scope of which is set forth in the appended claims. It is understood that modifications can be made in the procedures set forth without departing from the spirit of the invention.

Example 1

Oligonucleotide Synthesis

Oligonucleotide libraries were synthesized in a 1 µmole scale synthesis on an ABI 394 DNA synthesizer using standard automated solid phase DNA synthesis procedure and applying phosphoramidite chemistry. 1 µmole synthesis columns filled with 1000 A CPG support loaded with dA(Bz), dG(iBu), dC(Ac) or dT support (dA(Bz)-CPG (Sigma Aldrich, part no. A461010), dG(iBu)-CPG (Sigma Aldrich, part no. G461010), dC(Ac)-CPG (Sigma Aldrich, part no. C403001) and dT-CPG (Sigma Aldrich, part no. T461010) as well as standard dA(Bz), dC(Ac), dG(iBu) and dT phosphoramidites (Sigma Aldrich, part no. A111031, C113031, G111031, T111031) dissolved at a 0.1 M concentration in DNA grade acetonitrile as well as different pre-mixed phosphoramidite solutions consisting of two, three or four different bases were used as building blocks. The pre-mixed phosphoramidite solutions were prepared by dissolving each nucleoside phosphoramidite in DNA grade acetonitrile at a 0.1 M concentration and mixing same volumes of different nucleoside phosphoramidite solutions.

All other synthesis reagents as acetonitrile, dichloromethane, DCI activator, capping reagent A and B, oxidizer and detritylation reagent were standard synthesis reagents which are commercially available e.g. from Sigma Aldrich.

Standard DNA cycle was used for coupling dA, dG, dC and dT phosphoramidites as well as pre-mixed phosphoramidite solutions consisting of 2, 3 or 4 different bases. Cleavage of DMTon oligonucleotide library from the support as well as deprotection of protecting groups were performed by treatment of the support with AMA solution (conc. ammonia:40% aqueous methylamine 1:1) for 2 h at r.t. Crude DMT protected oligonucleotide library was evaporated and purified by RP-HPLC (column: PRP1 (Hamilton part no. 79352)) using 0.1 M triethylammonium acetate pH 7/acetonitrile gradient. Product fractions were combined and desalted by dialysis (MWCO 1000, SpectraPor 6, part no. 132638) against water for at least one day with at least 3 water changes thereby also cleaving DMT group. Finally, oligonucleotide library was lyophilized.

Typical yield for a 66 to 76mer containing 5 subsequent subsegments of all 4 different wobbles consisting of 3 different bases $(X1(dA/dG/dC)\text{-}X2(dA/dG/dT)\text{-}X3(dA/dC/dT)\text{-}X4(dG/dC/dT))_5$ was 100 to 140 OD260.

Oligonucleotide libraries were analyzed on the one hand by RP18 HPLC (Chromolith Performance RP18e, Merck, part number 1021290001) using 0.1 M triethylammonium acetate pH 7/acetonitrile gradient on the other hand by anion exchange HPLC (DNA Pak PA-100, Dionex, part number SP3815) using a 0.2 M-1.0 M sodium chloride gradient at alkaline pH (10 mM sodium hydroxide). Typical purities on both systems were 100%, on anion exchange system oligonucleotide library eluted as a rather broad peak.

Example 2

Optimization of Degenerated UID Sequences

A) Assumption:
1 µmol oligo synthesis scale with an estimated yield of 15% results in 150 nmoles of randomer which equals $9*10^{16}$ tagging molecules.

0.5 fmoles of a target DNA to be tagged are used per reaction which equals $3*10^8$ molecules per reaction.

Therefore, by dividing both numbers, 150 nmoles of randomer are available for $3*10^8$ tagging events, if 0.5 fmoles of target DNA are used per reaction.

B) UID sequences generated from multiple wobbles consisting of all 4 nucleotides N (A,G,C,T) according to prior art:

$N_{10}$:
A library having a $N_{10}$ wobble sequence contains $4^{10}$ or $10^6$ different sequences. 150 nmoles of such an oligonucleotide library contain $9*10^{16}/10^6=9*10^{10}$ identical sequences. This leads to $9*10^{10}/3*10^8=300$ identical sequences per reaction.

$N_{15}$:
A library having a $N_{15}$ wobble sequence contains $4^{15}$ or $10^9$ different sequences. A 150 nmoles of such an oligonucleotide library contains $9*10^{16}/10^9=9*10^7$ identical sequences. This leads to $9*10^7/3*10^8=0.3$ identical sequences per reaction.

Thus it is noted that a repeat of 10 wobbles consisting of 4 nucleotides does not guarantee tagging with unique sequences, a repeat of 15 wobbles consisting of 4 nucleotides would guarantee tagging with a unique sequence.

C) UID sequences generated from multiple wobbles consisting of only 3 nucleotides X:

$X_{16}$ (4 subsequent repeats of subsegments X1-X2-X3-X4):
A library having an $X_{16}$ wobble sequence contains $3^{16}$ or $4.3*10^7$ different sequences. 150 nmoles of such an oligonucleotide library contain $9*10^{16}/4.3*10^7=2.1*10^9$ identical sequences. This leads to $2.1*10^9/3*10^8=7$ identical sequences per reaction.

$X_{20}$ (5 subsequent repeats of subsegments X1-X2-X3-X4):
A library having an $X_{20}$ wobble sequence contains $3^{20}=3.5*10^9$ different sequences. 150 nmoles of such an oligonucleotide library contain $9*10^{16}/3.5*10^9=2.6*10^7$ identical sequences. This leads to $2.6*10^7/3*10^8=0.09$ identical sequences per reaction.

Thus a repeat of 16 wobbles consisting of 3 nucleotides does not entirely guarantee tagging with unique sequences, a repeat of 20 wobbles consisting of 3 nucleotides would guarantee tagging with a unique sequence.

Furthermore, it can be concluded that when conventional oligonucleotide synthesis is applied, an X20 sequence element comprising 5 subsequent repeats of subsegments X1-X2-X3-X4 is more than sufficient to guarantee for an individual labeling of a typical population of target nucleic acid molecules.

We claim:

1. A method for determining the sequences of a plurality of individual target nucleic acid molecules comprising the steps of:
   a. tagging each of said plurality of individual nucleic acid target molecules with an individual representative of a plurality of tagging oligonucleotides to generate a plurality of tagged individual target nucleic acid molecules, said plurality of tagging oligonucleotides:
      i. comprising at least $10^5$ individual representatives, each individual representative comprising a degenerated sequence segment,
      wherein the degenerated sequence segment comprises one or more identical subsegments having a sequence X1-X2-X3-X4,
      wherein X1 is a degenerated base region comprising a first set of three different bases or base analogs, X2 is a degenerated base region comprising a second set of three different bases or base analogs, X3 is a degenerated base region comprising a third set of three different bases or base analogs, and X4 is a degenerated base region comprising a fourth set of three different bases or base analogs, wherein said first, second, third and fourth sets are different from each other; and
      ii. not comprising an individual representative with a homopolymer stretch longer than 3 nucleotides in the degenerated sequence segment;
   b. amplifying said plurality of tagged individual target nucleic acid molecules, thereby generating amplified tagged individual target nucleic acid molecules; and
   c. sequencing said amplified tagged individual target nucleic acid molecules, thereby determining the sequences of the plurality of target nucleic acid molecules.

2. The method according to claim 1, wherein said plurality of individual target nucleic acid molecules comprise one or more identical nucleic acid analyte regions.

3. The method according to claim 2, further comprising a step of generating a consensus sequence for each of the one or more identical nucleic acid analyte regions from the sequences of the plurality of individual target nucleic acid molecules.

4. The method of claim 1, wherein the degenerated sequence segment comprises at least 2 subsegments.

5. The method of claim 4, wherein the degenerated sequence segment comprises at least 2 identical subsegments.

6. The method of claim 1, wherein the tagging is executed by ligating an individual representative of the plurality of tagging oligonucleotides to each of the plurality of individual target molecules.

7. The method of claim 1, wherein the tagging is executed by hybridizing a target binding site located downstream of the degenerated sequence segment of each individual representative of the plurality of tagging oligonucleotides to each of the plurality of individual target molecules.

8. The method of claim 7, further comprising elongating said plurality of tagging oligonucleotides by performing a target dependent DNA polymerase catalyzed primer extension reaction.

\* \* \* \* \*